(12) United States Patent
Suffin et al.

(10) Patent No.: US 8,239,013 B2
(45) Date of Patent: Aug. 7, 2012

(54) EEG PREDICTION METHOD FOR MEDICATION RESPONSE

(75) Inventors: Stephen C. Suffin, Sherman Oaks, CA (US); W. Hamlin Emory, Malibu, CA (US)

(73) Assignee: CNS Response, Inc., Aliso Viejo, CA (US)

( * ) Notice: Subject to any disclaimer, the term of this patent is extended or adjusted under 35 U.S.C. 154(b) by 1152 days.

(21) Appl. No.: 11/054,762

(22) Filed: Feb. 10, 2005

(65) Prior Publication Data

US 2005/0251419 A1    Nov. 10, 2005

Related U.S. Application Data

(63) Continuation of application No. 09/930,632, filed on Aug. 15, 2001, now abandoned, which is a continuation of application No. 09/148,591, filed on Sep. 4, 1998, now abandoned.

(60) Provisional application No. 60/058,052, filed on Sep. 6, 1997.

(51) Int. Cl.
*A61B 5/04* (2006.01)
(52) U.S. Cl. ............... 600/544; 600/300; 600/545
(58) Field of Classification Search ............ 600/300, 600/544, 558–559, 545; 705/2–3
See application file for complete search history.

(56) References Cited

U.S. PATENT DOCUMENTS

| | | | | |
|---|---|---|---|---|
| 4,201,224 A | * | 5/1980 | John | 600/544 |
| 4,533,346 A | * | 8/1985 | Cosgrove et al. | 604/66 |
| 4,632,122 A | * | 12/1986 | Johansson et al. | 600/383 |
| 4,846,190 A | * | 7/1989 | John | 600/544 |
| 5,083,571 A | * | 1/1992 | Prichep | 600/544 |
| 5,279,305 A | * | 1/1994 | Zimmerman et al. | 600/544 |
| 5,699,808 A | * | 12/1997 | John | 600/483 |
| 5,708,429 A | * | 1/1998 | Antoniol et al. | 341/65 |
| 5,730,146 A | * | 3/1998 | Itil et al. | 600/545 |
| 5,755,230 A | * | 5/1998 | Schmidt et al. | 600/544 |
| 5,775,330 A | * | 7/1998 | Kangas et al. | 600/544 |
| 5,791,342 A | * | 8/1998 | Woodard | 600/300 |

OTHER PUBLICATIONS

Suffin et al., "Neurometric Subgroups in Attentional and Affective Disorders and Their Association with Pharmacotherapeutic Outcome," 1995, Clinical EEG (Encephalography), Apr. 1995; 26(2): 76-83.*
Itil et al., 1990, "computer EEG Drug data Base in Psychopharmacology and in Drug Development," Psychopharmacology Bulletin 18(4): 165-172.*

* cited by examiner

*Primary Examiner* — Rene Towa
(74) *Attorney, Agent, or Firm* — Medlen & Carroll, LLP

(57) ABSTRACT

The present invention includes a system and method for computerized analysis of a patient's electroencephalogram (EEG) recorded by electrodes placed on the scalp, for the purpose of predicting patient response to medications and therapeutic agents commonly used in psychiatric practice. The prediction of the responses to medications (adverse, no effect, favorable outcome) is an important problem in the clinical practice of psychiatry. A growing number of therapeutic agents are available to the clinician but these agents generate variable responses when prescribed based solely on the patient's history and current symptoms. The present invention is used by physicians to improve patient outcome by selecting agents most likely to be effective for a given patient, using a standardized analysis of the digitized EEG and comparison of individual patient EEC data to a particular database of similar patients whose clinical outcome to pharmacotherapy is known.

18 Claims, 1 Drawing Sheet

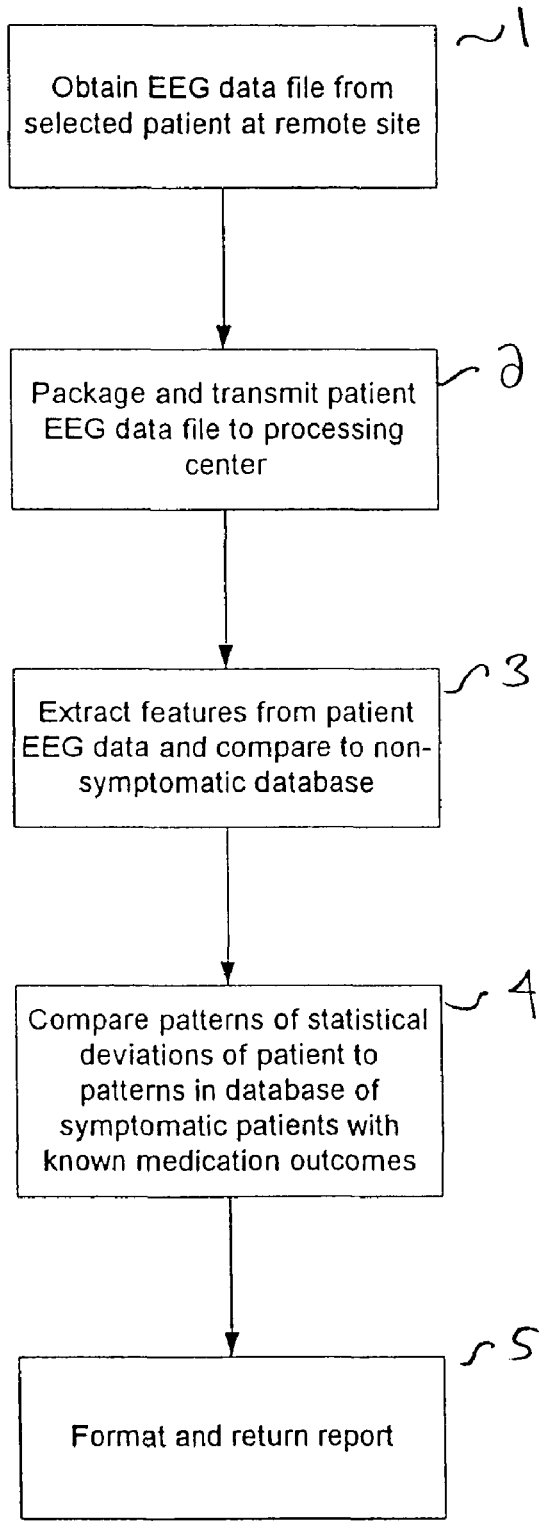

EEG PREDICTION METHOD FOR MEDICATION RESPONSE

CROSS REFERENCE TO RELATED APPLICATIONS

This is a Continuation of application Ser. No. 09/930,632 filed on Aug. 15, 2001 now abandoned which is a continuation of application Ser. No. 09/148,591 now abandoned filed on Sep. 4, 1998 which is a conversion of provisional application 60/058,052 filed on Sep. 6, 1997.

FIELD OF THE INVENTION

The field of this invention relates to systems and methods for transmitting digital EEG data and associated patient identifying information from a remote site to a central site, and for returning a report summarizing results of analyses and database comparison of the transmitted EEG, wherein the methods further comprise identifying a set of univariate and multivariate EEG features that when observed in a patient's EEG can be used to predict a favorable clinical responsive to psychoactive class medications

SUMMARY OF THE INVENTION

The methodology developed by the inventors, involves recording the EEG in a digital format from a patient diagnosed with a psychiatric disorder, the packaging and transmittal of the computer file containing the EEG and patient information to a report processing center via the Internet, generation of a probabilistically based medication responsivity report, and the return transmission of the report to the recording site via the Internet. EEG signals contained in computer files are not transmitted in real time but rather following the recording, "off-line".

The present invention includes a system for compressing, encrypting, tracking, and securely transmitting digital EEG data and associated patient identifying information from a remote site to a processing center, analyzing the EEG data with reference to a database of symptomatic individuals with known treatment outcomes in order to obtain therapy recommendations, and electronically returning a report summarizing results of analyses and database comparison all without requiring telephonic transmission.

In one embodiment the analysis methods of the present invention use an identified set of univariate and multivariate EEG features that when observed in a patient diagnosed with a psychiatric disorder, can be used with as part of rule-based classifier or selection method to predict a favorable clinical responses to individual medications and to various classes and combinations of medications, such as psychostimulant class medications, psychostimulant and antidepressant class medications, combinations of anticonvulsant and antidepressant class medications, combinations of psychostimulant, antidepressant, and anticonvulsant class medications.

The present invention also includes a method for computerized generation of clinical reports that integrates interpretive information from medical professionals with results of medication responsivity evaluation.

BRIEF DESCRIPTION OF THE FIGURES

The present invention may be understood more fully by reference to the following detailed description of the preferred embodiment of the present invention, illustrative examples of specific embodiments of the invention and the appended figures in which FIG. 1 illustrates a method of the present invention where: step 1 of FIG. 1 corresponds to elements 1 and 2 of the invention described below; step 2 corresponds to elements 3, 4, and 3; step 3 to elements 6 and 7: step 4 to element 8; and step 5 to elements 9 and 10.

DETAILED DESCRIPTION OF THE INVENTION

More specifically, the following steps are employed:
1) The EEG is recorded using electrodes placed on the patient's scalp, and the EEG data is stored in a digital format using a standardized protocol available on one of a number of commercially available instruments (current manufacturers include Cadwell Laboratories, Bio-Logic Systems Corp., Nicolet Biomedical, Oxford Instruments, among others). The International 10-20 System convention is used for determining the location of electrodes placed on the scalp. It is the responsibility of the recording facility to collect data in accordance with procedural specifications.
2) The following patient criteria apply:
   a) Patient must have received a psychiatric diagnosis as specified in the Diagnostic and Statistical Manual, currently the Fourth Edition (DSM-IV).
   b) Ages between six and ninety.
   c) Patient is taking no medications. All medications potentially influence the EEG and must be discontinued or avoided for seven half-lives prior to baseline EBG examination. This includes "over the counter" sleeping pills, pain medication, nutritional health supplements and mega-vitamins. agents are not excluded. Some cardiac agents are included in the reference population of after the age of fifty-five.
   e) Patients with any of the characteristics listed below are not suitable for prediction of medication responsivity based on EEG analysis:
      (i) intramuscular depo-neuroleptic therapy within the preceding twelve months
      (ii) a history of craniotomy with or without metal prostheses
      (iii) a history of cerebrovascular accident
      (iv) spikes or extreme low voltage on the conventional EEG
      (v) a current diagnosis of seizure disorder
      (vi) a diagnosis of dementia
      (vii) mental retardation
      (viii) current use of marijuana, cocaine, hallucinogens or other drugs of abuse
      (ix) inability to remain medication-free and drug-free for seven half-lives of the current agent(s) prior to EEG recording
      (x) significant abnormality of the CBC, chemistry or thyroid panel with TSH until corrected
   f) A "positive" Urine Drug Screen (UDS) interferes with medication prediction methods. Studies are processed only if the UDS is negative just prior to recording the digital EEG.
3) The digital EEG data computer file is packaged along with additional patient identifying information using packaging and transmission software. The patient information includes:
   a) name
   b) date of birth
   c) referring physician
   d) handedness e) height
f) weight
g) date of test
h) patient ID (social security number)
that it cannot be opened or examined by anyone other than at the processing center. The data transfer is rigorously secured to protect the confidentiality of patient records. The EEG files are encrypted at the recording facility with a key known only to processing center. The patient ID is transformed using a algorithm so that even in the case of mail routing error there is no way to associate the data with an individual. The data is compressed and protected with an additional password and data files are transmitted to a secure site. These steps mean that the patient data are protected against even purposeful attempts to intercept and read them.

The transmittal of the EEG file and related patient information is tracked as it is packaged, sent, processed, and returned. All log entries include dates and times calibrated to GMT.

The computer operating system preferred to run the packaging and report transmission software is currently Microsoft Windows 95/98. The following hardware and software is preferred:

Hardware Requirements
  Operating System: Windows 95 or Windows 98
  Processor: 486, 133 MHZ.
  Monitor and Video Card capable of displaying 256 colors.
  Disk Space: 35 MB
  RAM: 16 MB
  CD-ROM Drive if installing from CD-ROM
  Modem: 33.6 KBaud
  Internet Connection with approved Internet Service Provider
Software Requirements
  Adobe Acrobat Reader Version 3.01
  Microsoft Internet Explorer 4.0 or above
  The packaging and transmission software 4) The computer file is transferred off-hours using standard commercially available file transfer protocols (FTP) via the Internet, to a designated processing site. A special feature of the packaging and transmission software exists to allow immediate transfer of files for priority reporting if requested. The processing site monitors the transfer in order to detect professional interpretation, if requested, and specialized report generation.

5) The file is decompressed and decrypted at the processing site. Experienced technical and professional personnel then review the EEG signals and sections of the recording identified as containing signals generated by extracerebral sources are deleted from subsequent analyses. The samples of EEG selected for inclusion in analysis are then passed to the first stage of analysis.

6) The first stage of analysis includes computations that extract a standard set of features from the EEG. Quantitative spectral analysis provides commonly used measures of EEG power and relative power. Power is the square of amplitude; amplitude units are in microvolts ($\mu V$), power units are microvolts squared ($\mu V^2$). Relative power is a measure of the proportion of power in a given frequency band compared to the total band power at a given electrode. Frequency bands are defined as delta, 0.5-2.5 Hz.; theta, 2.5-7.5 Hz.; alpha, 7.5-12.5 Hz., and beta, 12.5-32 Hz. The total band is 0.5 to 32 Hz.

EEG coherence, a commonly used measure of the similarity of activity for a pair of two scalp electrodes, also is extracted by spectral analysis for all iterhemisplieric and intrahemispheric sets of electrode pairs, for each frequency band as defined above. Commonly used measures of peak frequency within each defined frequency band are computed.

Combinations of power and coherence measures over defined sets of scalp electrodes are also computed.

7) Features extracted from individual EEG data by quantitative spectral and statistical analysis are further compared to two distinct databases. In the second stage of analysis, Z-scores representing deviations from a nonsymptomatic reference population are computed. This reference population, often referred to as the "Neurometric" database, contains 2082 quantitative EEG measures including absolute power, relative power, coherence, symmetry, and mean frequency of the delta, theta, alpha and beta frequency bands of the EEG at every electrode position of the International 10-20 System for individuals from 6 to 92 years (database #1). The z-score value obtained by comparison of individual's data to the age appropriate subset of the database represents the patient's statistical deviation from the reference database.

patient database (database #2). This prediction is made by first identifying the pattern of EEG deviations from the reference database. Individual patient deviation is then compared with the characteristic features of the population of patients whose medications and treatment outcomes are known. A rule-based classifier is applied to estimate the likelihood that a patient EEG contains a pattern known to be responsive to a given agent, class of agents, or combination of agents or classes of agents. The EEG variables currently used by the classifier are shown in Tables 1-4, below.

| Column Heading Table 1 | Description of Abbreviation | Column Heading Table 2 | Description of Abbreviation |
|---|---|---|---|
| RMAD | Relative power monopolar anterior delta | FMAD | Frequency monopolar anterior delta |
| RMPD | posterior data | FMPD | posterior delta |
| RMAT | anterior theta | FMAT | anterior theta |
| RMPT | posterior theta | FMPT | posterior theta |
| RMAA | Anterior alpha | FMAA | anterior alpha |
| RMPA | Posterior alpha | PMPA | posterior alpha |
| RMAB | Anterior beta | FMAB | anterior beta |
| RMPB | posterior beta | FMPB | posterior beta |
| CEAD | Coherence interhemispheric anterior delta | AADL | Asymmetry interhemispheric delta—left |
| CEPD | Posterior delta | AADR | delta—right |
| CEAT | anterior theta | AATL | theta—left |
| CEPT | posterior theta | AATR | theta—right |
| CEAA | anterior alpha | AAAL | alpha—left |
| CEPA | Posterior alpha | AAAR | alpha—right |
| CEAB | Anterior beta | AABL | beta—left |
| CEPB | posterior beta | AABR | beta—right |
| AED | Asymmetry monopolar interhemispheric delta | CEBD | Coherence interhemispheric bipolar delta |
| NET | Theta | CEBT | Theta |
| ABA | Alpha | CEBA | Alpha |
| AEB | Beta | CEBB | Beta |
| AEBD | Asymmetry bipolar interhemispheric delta | RBDL | Relative power bipolar delta left |
| AEBT | Theta | RBDR | Delta—right |
| AEBA | Alpha | RBTL | Theta—left |
| AEBB | Beta | RBTR | Theta—right |
| CADL | Coherence intrahemispheric delta—left | RBAL | Alpha—left |
| CADR | Delta—right | RBAR | Alpha—right |
| CATL | Theta—left | RBBL | Beta—left |
| CATR | Theta—right | RBBR | Beta—right |
| CAAL | Alpha—left | | |
| CAAR | Alpha—right | | |

-continued

| Column Heading Table 1 | Description of Abbreviation | Column Heading Table 2 | Description of Abbreviation |
|---|---|---|---|
| CABL | Beta—left | | |
| CABR | Beta—right | | |

9) A formal report for the referring clinician is generated. The report is returned in a format that cannot be modified by the client (Adobe Systems, Inc., "portable document format", or "PDF"). This report contains certain elements as specifically requested by the referring clinician. These elements may include a professional medical interpretation of the digital EEG tracing, a presentation of selected features extracted by quantitative EEG analysis, a presentation of deviations from the Neurometric database, and a statement of the likelihood of favorable pharmacotherapeutic outcome based on comparison with patients having similar EEG features in the patient database #2. The treating physician is responsible for any medication selection, titrating of dosage and monitoring the patient for side effects and is instructed to incorporate results of reports with the psychiatric assessment to develop into an overall clinical treatment plan using the packaging and transmission software for viewing and printing the report by the client at the recording site. PDF files are opened and displayed using an interface to Adobe Acrobat Reader™ software. Reports may be printed on any operating system compatible printer.

11) Follow up EEG recordings can then be used to track changes produced by administration of medications by repeating the entire process outlined above. For follow up studies, the patient also is interviewed by the treating physician and Clinical Global Improvement (CGI) is scored. A score of −1 indicates an adverse effect, 0 no improvement, 1 minimal or mild improvement, 2 moderate improvement, and 3 marked improvement or remission of symptoms. The CGI scores are sent to the processing center and are reported along with changes, expressed as difference scores, on variables shown in Tables 1-4 above.

The invention described and claimed herein is not to be limited in scope by the preferred embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

The entire disclosures of references cited herein are incorporated herein, in their entireties, for all purposes.

Citation or identification of a reference in this application or in connection with this application shall not be construed that such reference is available as prior art to the present invention.

We claim:

1. A method, for electroencephalographic prediction of medication response comprising:
   a) providing:
      i) a patient located at a recording site, wherein said patient has been diagnosed with a psychiatric disorder;
      ii) a digital EEG file comprising electroencephalographic (EEG) data recorded from said patient;
      iii) a recording site computer system capable of transmitting said digital EEG file,
      iv) a receiving site computer system capable of receiving and processing said digital EEG file; and
      v) a first database comprising a plurality of multivariate EEG features classified within a plurality of age subsets of non-symptomatic reference individuals;
      vi) a second database comprising a plurality of multivariate EEG features associated with a plurality of various known medication classes and combinations of medications and a plurality of pharmacotherapeutic outcomes;
   b) transmitting said digital EEG file from said recording site computer system to said receiving site computer system;
   c) receiving and processing said digital EEG file with said receiving site computer system and said first database, wherein said processing generates a plurality of patient multivariate EEG features and a pattern of deviations between said plurality of patient multivariate EEG features and said first database, wherein said patient multivariate EEG features are extracted from at least one quantitative spectral analysis feature;
   d) comparing said pattern of deviations with said plurality of multivariate EEG features of said second database; and
   e) predicting a favorable clinical response of said patient to at least one of said plurality of various known medication classes and combinations of medications based upon said comparison.

2. The method of claim 1, wherein said patient, prior to said recording of step (a), has discontinued all medications for at least seven half-lives.

3. The method of claim 1, wherein said at least one quantitative spectral analysis feature comprises EEG absolute power, EEG relative power, EEG coherence, EEG symmetry and mean EEG frequency bands, wherein said frequency bands comprise alpha, beta, delta and theta.

4. The method of claim 1, wherein said method further comprises generating a report comprising said favorable clinical response prediction.

5. The method of claim 4, wherein said report further comprises a medical interpretation of said EEG data.

6. The method of claim 4, wherein said report further comprises a presentation of selected said quantitative spectral analysis features.

7. The method of claim 4, wherein said report further comprises a presentation of said pattern of deviations.

8. The method of claim 4, wherein said report further comprises a statement of the likelihood of favorable pharmacotherapeutic outcome based on said comparison of said pattern of deviations with said second database.

9. The method of claim 1, wherein said patient, first database, second database plurality of multivariate EEG features are selected from between relative power monopolar anterior delta (RMAD), relative power monopolar posterior delta (RMPD), relative power monopolar anterior theta (RMAT), relative power monopolar posterior theta (RMPT), relative power monopolar anterior alpha (RMAA), relative power monopolar posterior alpha (RMPA), relative power monopolar anterior beta (RMAB), and relative power monopolar posterior beta (RMPB).

10. The method of claim 1, wherein said patient, first database, and second database plurality of multivariate EEG features are selected from between coherence interhemispheric anterior delta (CEAD), coherence interhemispheric posterior delta (CEPD), coherence interhemispheric anterior theta (CEAT), coherence interhemispheric posterior theta (CEPT), coherence interhemispheric anterior alpha (CEAA), coherence interhemispheric posterior alpha (CEPA), coherence interhemispheric anterior beta (CEAB), and coherence interhemispheric posterior beta (CEPB).

11. The method of claim 1, wherein said patient, first database, and second database plurality of multivariate EEG features are selected from between frequency monopolar anterior delta (FMAD), frequency monopolar posterior delta (FMPD), frequency monopolar anterior theta (FMAT), frequency monopolar posterior theta (FMPT), frequency monopolar anterior alpha (FMAA), frequency monopolar posterior alpha (FMPA), frequency monopolar anterior beta (FMAB), and frequency monopolar posterior beta (FMPB).

12. The method of claim 1, wherein said patient, first database, and second database plurality of multivariate EEG features are selected from between asymmetry intrahemispheric delta-left (AADL), asymmetry intrahemispheric delta-right (AADR), asymmetry intrahemispheric theta-left (AATL), asymmetry intrahemispheric theta-right (AATR), asymmetry intrahemispheric alpha-left (AAAL), asymmetry intrahemispheric alpha-right (AAAR), asymmetry intrahemispheric beta-left (AABL), and asymmetry intrahemispheric beta-right (AABR).

13. The method of claim 1, wherein said patient, first database, and second database plurality of multivariate EEG features are selected from between asymmetry monopolar interhemispheric delta (AED), asymmetry monopolar interhemispheric theta (AET), asymmetry monopolar interhemispheric alpha (AEA), and asymmetry monopolar interhemispheric beta (AEB).

14. The method of claim 1, wherein said patient, first database, and second database plurality of multivariate EEG features are selected from between asymmetry bipolar interhemispheric delta (AEBD), asymmetry bipolar interhemispheric theta (AEBT), asymmetry bipolar interhemispheric alpha (AEBA), and asymmetry bipolar interhemispheric beta (AEBB).

15. The method of claim 1, wherein said patient, first database, and second database plurality of multivariate EEG features are selected from between coherence intrahemispheric delta-left (CADL), coherence intrahemispheric delta-right (CADR), coherence intrahemispheric theta-left (CATL), coherence intrahemispheric theta-right (CATR), coherence intrahemispheric alpha-left (CAAL), coherence intrahemispheric alpha-right (CAAR), coherence intrahemispheric beta-left (CABL), and coherence intrahemispheric beta-right (CABR).

16. The method of claim 1, wherein said patient, first database, and second database plurality of multivariate EEG features are selected from between coherence interhemispheric bipolar delta (CEBD), coherence interhemispheric bipolar theta (CEBT), coherence interhemispheric bipolar alpha (CEBA), and coherence interhemispheric bipolar beta (CEBB).

17. The method of claim 1, wherein said patient, first database, and second database plurality of multivariate EEG features are selected from between relative power bipolar delta-left (RBDL), relative power bipolar delta-right (RBDR), relative power bipolar theta-left (RBTL), relative power bipolar theta-right (RBTR), relative power bipolar alpha-left (RBAL), relative power bipolar alpha-right (RBAR), relative power bipolar beta-left (RBBL), and relative power bipolar beta-right (RBBR).

18. The method of claim 1, where said plurality of various known medication classes are selected from the group consisting of a psychostimulant class, a psychodepressant class, an anticonvulsant class and combinations thereof.

\* \* \* \* \*